United States Patent [19]
Proni et al.

[11] 3,963,148
[45] June 15, 1976

[54] APPARATUS FOR DRAWING, MEASURING AND DISCHARGING PROPORTIONAL AMOUNTS OF FLUID

[75] Inventors: Oscar Proni, Hollywood; Loran Vinson Melnick; William Taylor Henderson, both of Miami, all of Fla.

[73] Assignee: Coulter Electronics, Inc., Hialeah, Fla.

[22] Filed: Mar. 12, 1975

[21] Appl. No.: 557,681

Related U.S. Application Data

[63] Continuation-in-part of Ser. No. 432,348, Jan. 10, 1974, abandoned.

[52] U.S. Cl. .............................. 222/132; 222/134; 222/137; 23/259
[51] Int. Cl.² ........................................ B67D 5/60
[58] Field of Search .......... 222/132, 134, 137, 135, 222/136; 23/253 R, 259

[56] References Cited
UNITED STATES PATENTS

| | | | |
|---|---|---|---|
| 3,127,062 | 3/1964 | Feichtmeir et al. | 222/135 |
| 3,401,839 | 9/1968 | Christie | 222/137 |
| 3,484,207 | 12/1969 | Anthon | 222/135 X |
| 3,525,592 | 8/1970 | Buckley | 222/135 |
| 3,655,094 | 4/1972 | Hobbs | 222/135 |
| 3,800,984 | 4/1974 | Phelan | 23/259 R |
| 3,837,534 | 9/1974 | Natelson | 222/137 |

*Primary Examiner*—Allen N. Knowles
*Attorney, Agent, or Firm*—Silverman & Cass, Ltd.

[57] ABSTRACT

An automatic diluting device draws and dispenses a volume of sample along with a volume of diluent so as to maintain a precise ratio between the volume of sample and the volume of diluent. The device includes a diluent chamber having a plunger therein which is reciprocable between a first and second position for displacing a first volume therein when moved, and at least a first sample chamber having a plunger therein reciprocable between a first and second position for displacing a second volume therein when moved. The first and second volumes are arranged to have a fixed precise ratio with respect to one another for any equal distance moved by said first and second plungers in their chambers. A coupling device couples the plungers together for simultaneously reciprocally moving the plungers an equal distance in the chambers between first and second positions. Reciprocal movement of the plungers between the first and second positions causes a volume of sample and a volume of diluent to be drawn into the device, then both expelled at a common point for allowing mixing of the diluent and sample.

27 Claims, 13 Drawing Figures

APPARATUS FOR DRAWING, MEASURING AND DISCHARGING PROPORTIONAL AMOUNTS OF FLUID

REFERENCE TO RELATED APPLICATION

This application is a continuation-in-part of copending application Ser. No. 432,348 filed Jan. 10, 1974, now abandoned, and owned by the same assignee as this application.

BACKGROUND OF THE INVENTION

In the analysis and study of body fluids, the fluids to be studied are generally diluted in order to carry out the analytical procedures on diluted samples. In many cases, the diluting operation is performed manually, using a standard calibrated pipette. This manual procedure is time consuming and tedious in addition to presenting a great opportunity for error, especially where a high degree of skill has not been attained by the technician, and where a high speed of operation is necessary or desirable. Mechanical diluters have been used successfully for a number of years. Examples of such devices are shown and described in U.S. Pat. Nos. 3,138,290 and 3,138,294.

Efforts have been made to develop semiautomatic electromechanical devices for performing diluting operations. One such device is shown and described in U.S. Pat. No. 3,446,400, issued May 27, 1969 to J. C. Hobbs II et al. Although semiautomatic electromechanical diluters have been used successfully for a number of years, these devices tend to be cumbersome, and complicated. In the Hobbs device, a motor driven eccentric and yoke assembly are arranged to shift downwardly and upwardly the piston of a fixed volume diluent chamber for drawing and discharging a measured amount of diluent. As the yoke assembly approaches its lower position, it engages and drives downwardly the piston assembly of a sample chamber communicating with an uncalibrated pipette, thus drawing a volume of sample into the pipette. As the yoke assembly is then upwardly moved, the sample and diluent are discharged through the pipette.

The ratio of sample volume to diluent volume must be precisely maintained in order to allow correct statistical evaluation and analysis of the diluted samples. Movement of the piston assembly in the sample chamber must be precisely synchronized with movement of the yoke assembly and the piston of the fixed volume diluent chamber in order to achieve a precise ratio of sample and diluent. This synchronization is achieved via adjustable stops attached to the piston assembly of the sample chamber and to adjustments possible on the yoke assembly itself. A loosening of these adjustments, or a wearing away of any of the parts so as to produce greater movement of one piston relative to the other in response to movement of the yoke, will cause a change in ratio of sample volume to diluent volume. Frequent adjustments of these limits and stops have been required in order to maintain a reasonable degree of accuracy for the mechanical diluter. These frequent adjustments are unnecessarily time consuming and expensive, as well as reducing the amount of time during which the mechanical diluter may be employed and creating a serious and substantial source of error.

Semiautomatic electromechanical diluters designed to satisfy most user requirements are further complicated in that they must provide a plurality of different precise dilution ratios by simple switch selection. In general, prior efforts to develop a diluter which may be operated to selectively provide one of a plurality of precise dilution ratios have been unsuccessful or have resulted in a device such as described above and having all of the problems noted above.

SUMMARY OF THE INVENTION

In practicing this invention, an automatic diluting device is provided for drawing a volume of sample and a volume of diluent and mixing the sample and diluent in one of a plurality of precisely controlled ratios. The device includes a diluent chamber having a first plunger therein which is reciprocable between a first and second position for displacing a first volume in the chamber when the first plunger is moved in the chamber. First and second sample chambers are also provided having second and third plungers respectively positioned in the chambers and reciprocable between the first and second position for displacing a second and third volume respectively in the chambers when moved therein. The first and second volumes and first and third volumes are arranged to have a fixed precise ratio with respect to one another for any equal distance moved by the three plungers in their chambers. A motor driven coupling device is secured to all three plungers for simultaneously reciprocally moving them an equal distance in their chambers between the first and second positions. A sample intake and discharge passage, including an uncalibrated pipette, is coupled through a switching valve assembly to one of the first and second chambers for drawing a sample into the pipette during movement of the second and third plungers between the first and second positions and for discharging the sample during movement of the second and third plungers between the second and first positions. A diluent intake passage is coupled to the diluent chamber for drawing diluent into the chamber during movement of the first plunger between the first and second positions, and a diluent discharge passage, including a discharge nozzle, is coupled to the diluent chamber for discharging diluent from the chamber during movement of the first plunger between the second and first positions. Some of the diluent from the diluent chamber is also coupled through the switching valve assembly to the selected one of the first or second sample chambers in order to discharge a small amount of diluent through the uncalibrated pipette in addition to discharging the sample. The sample chamber which is not selected is also connected via the switching valve assembly to a source of diluent for filling and emptying the sample chamber with diluent in response to movement of the plunger between the first and second and second and first positions, thus preventing damage to the chamber due to excessive vacuum conditions.

Alternately in practicing this invention an automatic diluting device is provided for drawing a volume of sample and a volume of diluent and mixing the sample and diluent in a precise ratio. The device includes a diluent chamber having a first plunger therein which is reciprocable between a first and a second position for displacing a first volume in the chamber when the first plunger is moved. A first sample chamber also is provided having a second plunger therein which is reciprocable between a first and a second position for displacing a second volume in the chamber when the second plunger is moved. The first and second volumes are arranged to have a fixed precise ratio with respect to one another for any equal distance moved by the plungers in their chambers. A sample intake and discharge passage is coupled to the first sample chamber for drawing a sample therein during movement of the second plunger between the first and second positions and discharging the sample during movement of the second plunger between the second and first positions. A diluent intake passage is coupled to the diluent chamber for drawing diluent therein during movement of the first plunger between the first and second position. A diluent discharge passage is coupled to the diluent chamber for discharging diluent during movement of the first plunger between the second and first positions. A valve is coupled to the diluent chamber, the diluent intake passage, the diluent discharge passage and the sample intake and discharge passage. The valve is operative during movement of the first plunger between the first and second positions to couple the diluent chamber to the diluent intake passage. During movement of the first plunger between the second and first positions the valve is operative to couple the diluent chamber to the diluent discharge passage and to couple the diluent discharge passage to the sample intake and discharge passage, thus expelling sample and diluent and washing the sample from the sample intake and discharge passage.

DESCRIPTION OF THE PREFERRED EMBODIMENT

Figure 1:
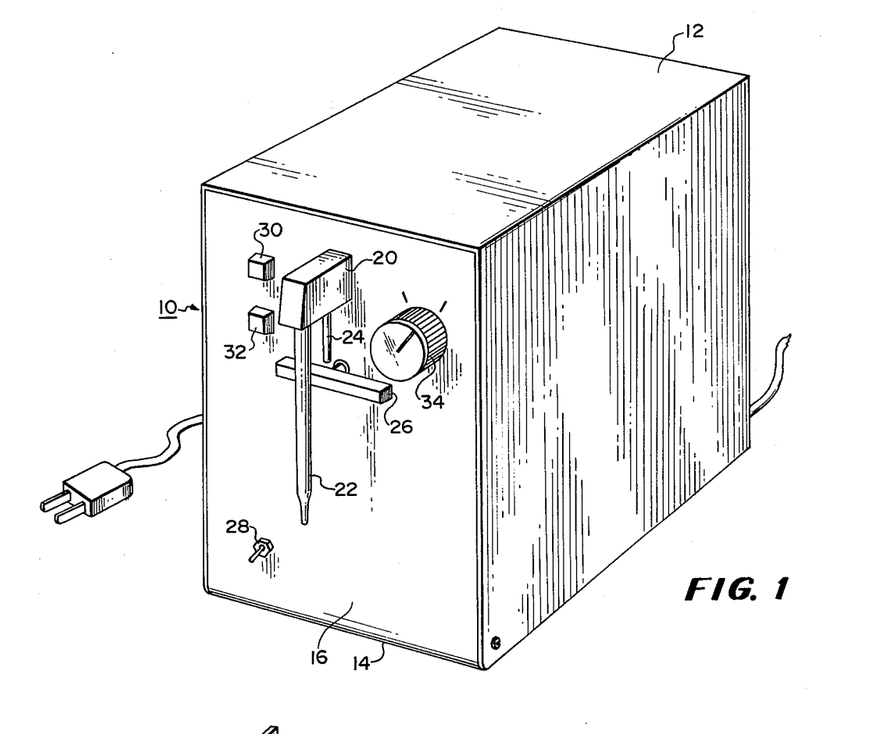
FIG. 1 is a perspective view of the diluter of this invention showing the front, top and one side.

Referring to FIG. 1, the number 10 generally designates the diluter of this invention having a housing composed of two interfitting housing sections 12 and 14. Housing section 12 defines the top, rear and side walls, and housing section 14 defines the bottom, front wall 16, and a small upwardly extending rear lip 18. A mounting block 20, with two separated fluid paths or conduits bored therethrough and shown in the figure by dotted lines, is secured to front wall 16 of housing section 14. An uncalibrated pipette 22 is connected to one of the fluid paths in mounting block 20 and extends downwardly; and a nozzle 24 is connected to the second fluid path in mounting block 20 and also extends downwardly, but for a shorter distance than pipette 22. A switch actuator 26 extends through front wall 16 and is positioned between pipette 22 and wall 16. Switch actuator 26 is pushed towards front wall 16 in order to actuate a sample and diluent intake cycle and a sample and diluent discharge cycle.

Power switch 28 is also positioned on front wall 16 for turning the diluter 10 on and off. Status lamp 30 lights up to indicate that the diluter is in, or will begin the sample and diluent intake cycle, and status lamp 32 lights up to indicate that the diluter is in or will begin the sample and diluent discharge cycle. Dilution knob 34 in the preferred embodiment allows selection of one of two precise dilution ratios by movement of the dilution knob 34 to one of the two indexing positions shown.

A vertically and rearwardly extending member 36 (FIG. 2) is secured to housing section 14 and mounts most of the diluting mechanisms employed in diluter 10. Referring to FIG. 4, an electric motor 38 is secured to one side of member 36 and is shown partially cut away in order to clearly show an aperture 40 formed in member 36. A rotating drive member 42 of motor 38 extends through aperture 40. A cam 44 is secured to the rotating drive member 42 and has eccentrics 46 and 48 mounted on one side thereof as shown in FIG. 4, and eccentric 50 mounted on the other side and shown in FIGS. 2, 3, 7, 8, 9 and 10. Microswitch 52, mounted to member 36 consists of a single normally closed contact for supplying power to motor 38. This normally closed contact is opened, thus interrupting rotation of motor 38 when either one of cams 46 or 48 strike lever 54 of microswitch 52. Actuation of switch actuator mechanism 26 causes a normally open contact in microswitch 56, secured to member 36, to close, paralleling the normally closed contact of microswitch 52 and again supplying power to motor 38 to enable rotation thereof. When motor 38 has rotated sufficiently to move either one of eccentrics 46 or 48 away from lever 54, allowing closure of the normally closed contact in microswitch 52, switch actuator mechanism 26 may be released and motor 38 will continue to rotate until the eccentric again interrupts microswitch 52. A status control microswitch 58 is also secured to member 36 and includes a lever (not shown) such as lever 54 extending through an aperture in member 36 (not shown), similar to aperture 40 is member 36. The lever will contact portions of the diluter mechanism as, hereinafter described in greater detail, causing microswitch 58 to switch power between status lamps 30 and 32 for lighting the status lamps in accordance with the operating cycle of the diluter 10.

Figure 2:
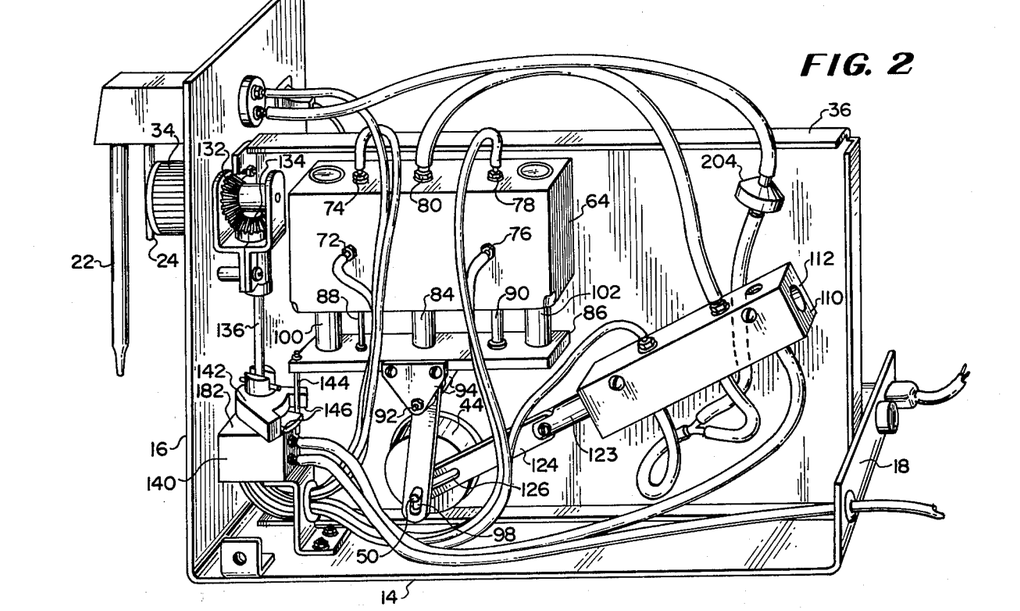
FIG. 2 is a perspective view of the diluter of this invention with the cover off, showing the diluting mechanisms.
Figure 3:
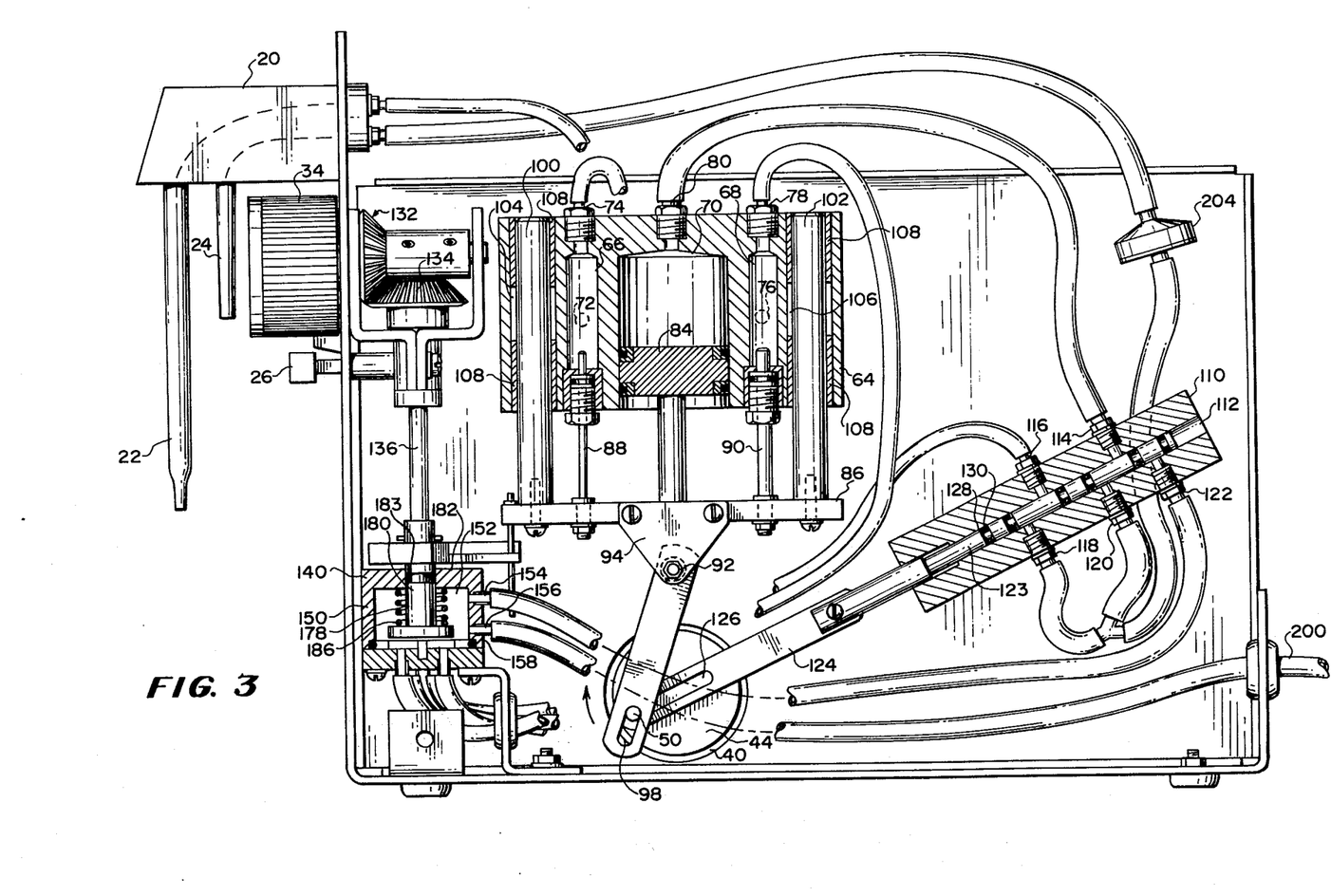
FIG. 3 is a plan side view of the diluter of this invention with the cover off showing various parts of diluter mechanisms in section.
Figure 4:
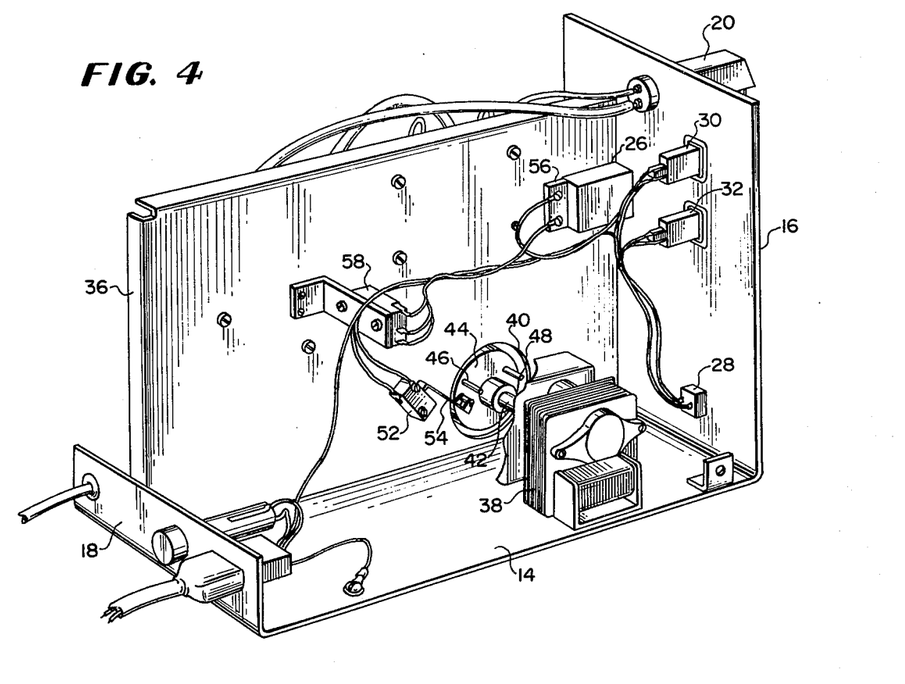
FIG. 4 is a perspective view of the diluter of this invention with the cover off showing the motor and other electrical mechanisms.

Referring now to FIGS. 2 and 3, a chambered block 64 is secured to member 36. Chambered block 64 has a sample chamber 66, a sample chamber 68 and a diluent chamber 70 formed therein. Sample chamber 66 has entry and exit ports 72 and 74 communicating therewith through chambered block 64; sample chamber 68 has entry and exit ports 76 and 78 communicating therewith through chambered block 64; and diluent chamber 70 has entry and exit port 80 communicating therewith through chambered block 64.

Diluent chamber 70 is precisely formed in chambered block 64 so as to displace a predetermined and precise volume in response to movement of plunger 84 a predetermined distance within diluent chamber 70. That is, diluent chamber 70 is formed having a diameter which is precisely controlled so that an upward movement of piston 84 in diluent chamber 70 of for example one-half inch will displace a fixed precise volume within diluent chamber 70. In the preferred embodiment, the diameter of chamber 70 is controlled to within 4/1,000ths of an inch. Piston 84 is reciprocable in diluent chamber 70 and is secured at its bottom end to a mounting plate 86.

Plungers 88 and 90 are secured at their bottom ends to mounting plate 86 and have the upper portions thereof extending into sample chambers 66 and 68 respectively. Plungers 88 and 90 are reciprocable in sample chambers 66 and 68 respectively and have precisely formed diameters such that for any predetermined length, each will define and displace a specific volume. In the preferred embodiment the diameter of plunger 88 is controlled to within 2/10,000ths of an inch, and plunger 90's diameter is controlled to within 1/1,000ths of an inch. Reciprocal movement of either plunger 88 or 90 in sample chamber 66 and 68 respectively, therefore, will displace a precise volume within sample chambers 66 and 68. The diameter of plunger 88 is selected such that the volume displaced in chamber 66 by movement of plunger 88 a predetermined distance in chamber 66, for example ½ inch, will be precisely equal to 1/500ths of the volume displaced by movement of piston 84 in diluent chamber 70 for an equal distance of ½ inch. The diameter of plunger 90 is selected such that the volume displaced in chamber 66 by movement of plunger 90 a predetermined fixed distance within chamber 66 will be precisely equal to 1/100ths of the volume displaced by movement of piston 84 in diluent chamber 70 for an equal distance.

A pivot pin 92 is fixedly secured beneath mounting plate 86 via positioning plates 94. A pivot arm 96 has one end pivotally secured to pivot pin 92 and has an elongate slot 98 at its other end in which is fixed eccentric 50 on rotating cam 44. The rotation of cam 44 and eccentric 50 in response to operation of the motor 38 will cause pivot arm 96 to follow eccentric 50 thereby reciprocally moving mounting plate 86 up and down between a first and second position in response to ½ cycle of rotation of eccentric 50 and between the second and first position in response to the other ½ cycle of rotation of eccentric 50 and cam 44. Elongate slot 98 allows for some lost motion as between the rotation of eccentric 50 and the reciprocal movement of plate 86. That is, plate 86 will only be urged upward or downward during certain portions of the rotational cycle of eccentric 50 because of the elongate slot 98 at one end of pivot arm 96.

Guide rods 100 and 102 have one end secured to the upper surface of mounting plate 86 and extend vertically upward through guide bores 104 and 106 respectively in chambered block 64. Four bushings 108, positioned in guide bores 104 and 106 allow reciprocal movment of guide rods 100 and 102 therein thus maintaining the plane of mounting plate 86 correctly aligned perpendicular to the axis of chambers 66, 68 and 70. This will cause plungers 88, 90 and 84 to move equal distances in their respective chambers in response to reciprocal movement of mounting plate 86 so that the ratio of volumes displaced by plungers 88 and 84 or 84 and 90 will always remain precisely the same. This ratio will remain the same notwithstanding the changes in total distance traveled by mounting plate 86. The distance traveled by mounting plate 86 therefore will only effect the total quantity or total volume displaced by the plungers and not the ratio of volumes displaced.

A spool valve housing 110 is secured to member 36. Spool valve housing 110 has a bore 112 extending therethrough. Five entry and exit ports 114, 116, 118, 120 and 122 communicate with bore 112 through the sides of spool valve housing 110. Bore 112 slidably receives an elongated spool valve member 123. Spool valve member 123 is a rod having sufficient clearance in bore 112 to allow fluid to flow around the rod in bore 112. The rod has circumferential grooves 128 cut therein into which are placed sealing O-rings 130. O-rings 130 act to provide a seal between the wall of bore 112 and spool valve member 123 such that fluid cannot pass along the axis of the bore from one side of an O-ring to the other. Spool valve member 123 may be slidably moved to two positions in spool valve housing 110 as most clearly represented in FIGS. 7 and 9. In the first position, shown in FIG. 7, entry and exit ports 114 and 122 are in communication with one another, and entry and exit ports 116, 118 and 120 are blocked. For the second position, shown in FIG. 9, entry and exit ports 116 and 118 are in communication with one another, entry and exit ports 114 and 120 are in communication with one another, and entry and exit port 122 is blocked. A pivot arm 124 has one end pivotally secured to an end of spool valve member 123 and an elongate slot 126 in the other end in which is fixed eccentric 50. Rotation of cam 44 and eccentric 50 in response to operation of the motor 38, will cause pivot arm 124 to reciprocate during at least a portion of the rotational cycle of eccentric 50 and cam 44. The reciprocal motion of pivot arm 124 will cause spool valve member 122 to reciprocate between the above noted first and second positions during certain portions of the rotational cycle of eccentric 50. Spool valve member 123 moves during only certain portions of the rotational cycle of eccentric 50 because the elongate slot 126 allows for some lost motion as between the rotation of eccentric 50 and the reciprocal movement of pivot arm 124.

As previously noted, diluter 10 is capable of providing either one of two dilution ratios by simply setting dilution knob 34. Dilution knob 34 is attached via a shaft (not shown) to bevel gears 132 and 134 for translating the horizontally directed rotational motion to vertically directed rotational motion. A shaft 136 secured to bevel gear 134 transfers this vertically directed rotational motion to a switching valve assembly 140. A cam 142 is secured to shaft 136. Cam 142 engages a guide pin 144 secured to and extending downwardly from mounting plate 86, at the extremes of rotation of knob 34 and cam 142, in order to prevent knob 34 and therefore shaft 136 from being turned beyond the desired index positions. Notches 146 in cam 142, at the extremes of rotation of cam 142, allowed pin 144 to pass therethrough the notches 146 prevent knob 34 from being rotated, and switching valve assembly 140 from being changed when mounting plate 186 is in its lower or second position and ½ of the diluter cycle has occurred. When a cycle is to be initiated, mounting plate 86 is in the first or upper position such that pin 144 will not extend into notches 146 allowing rotation of knob 34 and shaft 136.

Figure 5:
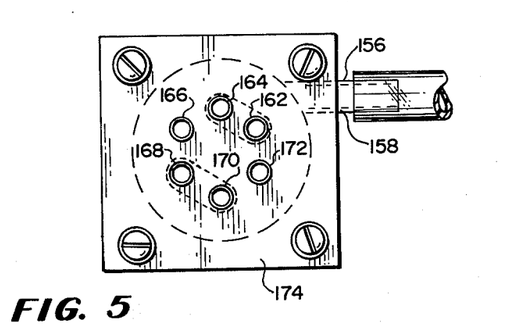
FIG. 5 is a plan view of the face of the switching valve assembly of this invention.
Figure 6:
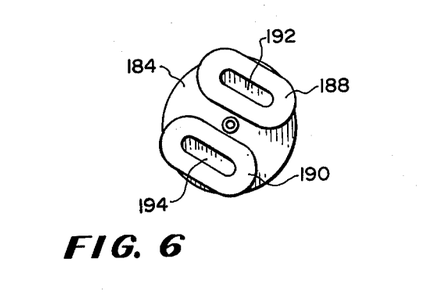
FIG. 6 is a plan view of the piston in the switching valve assembly of this invention.

Switching valve assembly 140 is shown in FIGS. 2 and 3 and portions thereof are shown in FIGS. 5 and 6. Switching valve assembly 140 in the embodiment shown includes a cube shaped housing 150 defining a central chamber 152. Entry ports 154 and 156 are formed in one side wall 158 of housing 150 and communicate with central chamber 152. A series of six switchable entry ports 162, 164, 166, 168, 170 and 172, are formed in bottom wall 174 of housing 150 and arranged in a circle. Each one of the switchable entry ports communicates with central cavity 152. A switching valve rotor assembly 178 is positioned in central cavity 152 and includes a rod shaped portion 180 which extends out of housing 150 through an aperture in top wall 182. Sealing rings 184 prevent seepage from central chamber 152. A second circular plate portion 184 of switching valve rotor assembly 178 is secured to an end of rod portion 180 and is held firmly against bottom wall 174 via springs 186. A pair of oval shaped rubber grommets 188 and 190 are secured to the bottom surface of circular plate portion 184 of switching valve rotor assembly 178 as is best shown in FIG. 6. Grommets 188 and 190 are formed from silicon rubber and have a hardness of approximately 60 or 70 on the SHORE SCARE. Oval shaped grommets 188 and 190 define cavities 192 and 194 respectively. The cavities 192 and 194 are positioned such that they will communicate with two switchable entry ports simultaneously, thus providing a channel or conduit between those two entry ports. For example, with switching valve rotor assembly 178 positioned as shown in FIGS. 5 and 6 cavity 192 in oval shaped grommet 188 will provide a conduit between switchable entry ports 162 and 164, while cavity 194 in oval shaped grommet 190 will provide a conduit between switchable entry ports 168 and 170. This of course would be the location of cavities 192 and 194 with knob 34 set for one dilution ratio. With knob 34 set for the other dilution ratio, circular plate portion 184 of switching valve rotor assembly 178 would be rotated 60°, causing cavity 192 to interconnect switchable entry ports 162 and 172, and causing cavity 194 to interconnect switchable entry ports 166 and 168. Because oval shaped grommets 188 and 190 are formed from silicon rubber, and are of a hardness of 60 to 70 on the SHORE SCALE, they can be easily rotated the required 60° without deforming, and will still maintain a seal so as to prevent any fluid passing through cavities 192 and 194 from escaping into the central chamber 152. The two switchable entry ports which do not communicate with one another via cavities 192 and 194 are in communication with central chamber 152 of switching valve assembly 140.

FIGS. 7 through 10 illustrate the diluter 10 in various operational states. It is to be assumed, that flexible tube 200 is in communication with a source of water or other suituable diluent, and that diluter 10 has been primed a number of times so that the passages of the flexible tubes shown in the drawings interconnecting chambered block 64, spool valve housing 110, switching valve assembly 140 and mounting block 20 and chambers 66, 68, and 70, central cavity 152 and the appropriate sections of spool housing 110 are all filled with diluent.

Prior to commencement of operation of the device, the operator rotates diluent selection knob 34 into either one of its two positions to select the particular volume of sample to be diluted by a fixed volume of diluent. In the embodiment shown in FIGS. 7 through 10, the ratio of sample volume to diluent volume selected is 1/100ths. Thereafter, a suitable beaker containing the liquid sample to be diluted is raised until the tip of the pipette 22 is immersed in the sample. Switch actuator mechanism 26 is then depressed to close the contacts of microswitch 56. This supplies power to motor 38, beginning rotation of motor 38 and of rotating drive member 42. Rotation of member 42 causes rotation of cam 44 and eccentric 50 in a clockwise direction, with eccentric 50 starting in the position as shown in FIG. 7, it is at the end of elongate slot 98 in pivot arm 96 so that any additional clockwise movement of eccentric 50 will cause downward movement of plate 86 and plungers 84, 88 and 90.

The downward movement of plunger 84 creates a vacuum in chamber 70 causing diluent to be drawn from a source of diluent through flexible tubing 200, into and out of ports 156 and 154 respectively in switching valve assembly 140, into and out of ports 122 and 114 respectively in spool valve housing 110, and through port 80 into diluent chamber 70. The downward movement of plunger 90 creates a vacuum in chamber 78 which is communicated via entry and exit port 78, switchable entry port 164, cavity 192, switchable entry port 162, a fluid path in mounting block 20 and pipette 22, causing a quantity of the sample to be drawn into uncalibrated pipette 22. The quantity of sample drawn into pipette 22 will be equal to the volume displaced by movement of plunger 90. Downward movement of plunger 88 also creates a vacuum in chamber 66. This vacuum will be communicated via exit and entry port 74, switchable entry port 172, entry port 156 of switching valve assembly 140 and flexible tubing 200 to the source of diluent, drawing the diluent into sample chamber 66. Diluent is drawn into sample chamber 66 when the chamber is not being used to obtain a particular volume of sample, in order to prevent excessive vacuum from being developed in the chamber 66 which could adversely affect or damage the seals and seriously jeopardize subsequent operation of the diluter.

Figure 7:
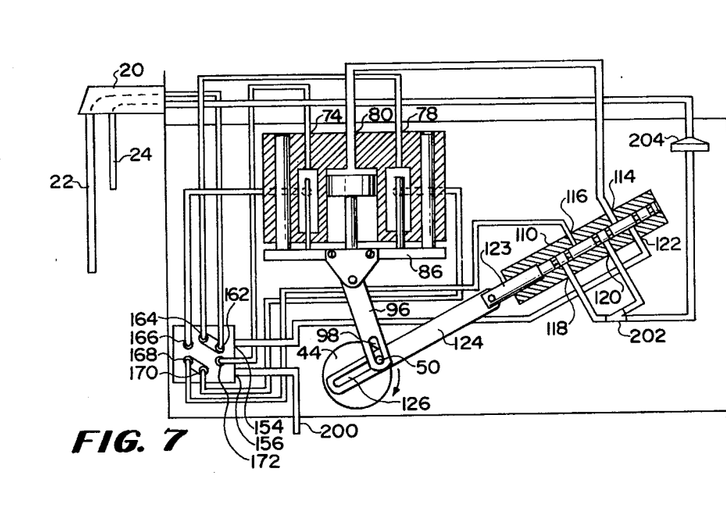
FIG. 7 is a plan interconnection and partial section view of the diluter mechanisms showing the diluter in a first stage of its operation.
Figure 8:
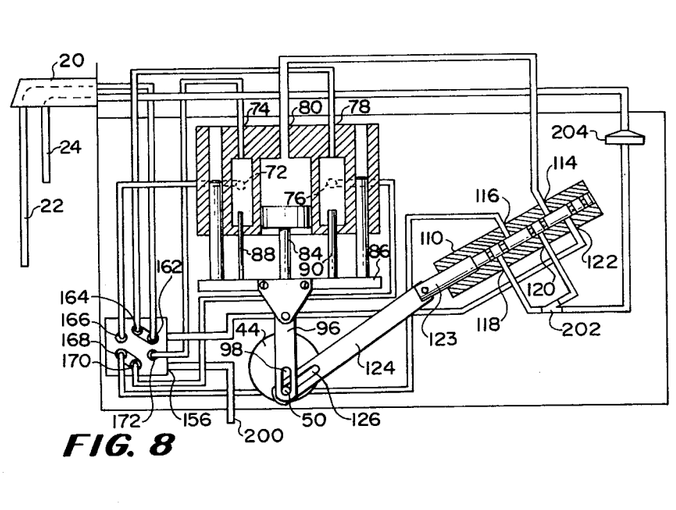
FIG. 8 is a plan interconnection and partial section view of the diluter mechanism showing the diluter in a second stage of its operation.

During the portion of the rotational cycle of eccentric 50 shown as occurring between the positions in FIGS. 7 and 8, spool valve member 123 remains stationary in the first position because pivot arm 124 is freely slidable on eccentric 50 as a result of the elongate slot 126. However, when eccentric 50 reaches the point of rotation shown in FIG. 8 and continues rotating in a clockwise direction, it will engage the end of elongate slot 126 causing pivot arm 124 to be moved in response to continued rotation of eccentric 50, thus moving spool valve member 123 to the second position. This second position will be reached and no further movement will occur when eccentric 50 is in the position shown in FIG. 9. It should be noted in addition at this point that between the positions of eccentric 50 shown in FIG. 8 and FIG. 9 and during movement of spool valve member 123, there will be no additional upward or downward movement of plate 86 and plungers 84, 88 and 90.

Figure 9:
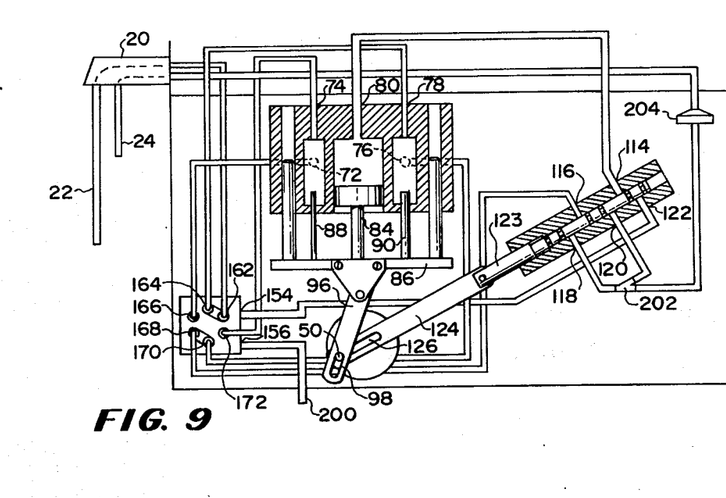
FIG. 9 is a plan interconnection and partial section view of the diluter mechanisms showing the diluter in a third stage of operation.

When the position shown in FIG. 9 has been reached by rotation of motor 38, one of cams 46 and 48 on the reverse side of member 36 will engage lever 54 opening the contacts supplying power to motor 38 and automatically stopping the operation. No additional sample or diluent will be drawn into diluter 10. The operator may now withdraw the beaker from the tip of pipette 22, and preferably wipe the tip of pipette 22 to remove any liquid clinging to the outer surface and the lower end thereof. Thereafter, a receptacle (not shown), suitable for receiving the diluted sample is placed beneath pipette 22 and nozzle 24 and switch actuator mechanism 26 is again actuated to close the contacts of microswitch 56. This manually overrides the opening of the contacts in microwitch 52 causing motor 38 and rotating drive member 42 to again begin clockwise rotation. At this point as shown in FIG. 9, eccentric 50 is at the upper end of elongate slot 98 in pivot arm 96 and additional clockwise rotation will begin to cause mounting plate 86 to move upwardly. This upward movement will continue until eccentric 50 reaches the point shown in FIG. 10. During this upward movement, plungers 84, 88 and 90 will move upward an equal distance each displacing a precise volume of sample diluent determined by the distance moved by the plungers. The ratio of displacement between sample chamber and plunger 90 and diluent chamber and plunger 84 will be maintained at precisely 1/100 notwithstanding any variations in the total volume displaced due to the distance moved by mounting plate 86. This, as previously noted, is due to the precise diameter ratios between chamber 70 and plungers 88 and 90. During this upward movement of mounting plate 86 and plunger 90, the diluent displaced in chamber 68 will exit via entry and exit port 78, pass into switchable entry port 164, through cavity 192 and out of switchable entry port 162 in switching valve assembly 140, through the fluid path in mounting block 20 and pipette 22, forcing the entire sample drawn into pipette 22 out of the pipette. Because of the relatively restricted aperture size of the end of pipette 22 the sample will be discharged at a relatively high velocity during the period of time taken for this portion of the cycle.

Figure 10:
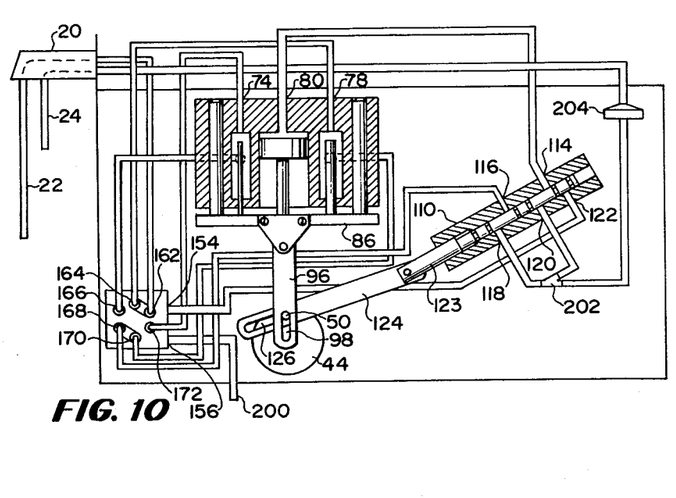
FIG. 10 is a plan interconnection and partial section view of the diluter mechanisms showing the diluter in a fourth stage of its operation.

During the upward movement of plunger 84 in chamber 70 the diluent displaced will be expelled via entry and exit port 80, and through entry and exit ports 114 and 120 in spool valve housing 110. At the entry and exit port 120 of spool valve housing 110 the discharging diluent will take two paths as shown via a Y connection 202. The first path is from Y connection 202 through one way check valve 204, through a fluid conduit in mounting block 20, and out through nozzle 24 into the receptacle. The aperture at the end of nozzle 24 is substantially larger than the aperture at the end of pipette 22. This allows a much larger volume of diluent to be discharged through nozzle 24 than can be discharged through nozzle 22 in the same period of time. Furthermore, the diluent will be discharged at a much lower velocity, thus preventing the formation of bubbles in the diluted sample. If the diluent and sample were to be discharged from a single nozzle or pipette as was done in the prior art, the discharge would have to be accomplished much more slowly such as for example by use of plurality of reduction gears coupled to motor 38, or it would create bubbles in the diluted sample which are undesirable.

The second path is from Y connection 202 into and out of entry and exit ports 118 and 116 of spool valve housing 110, into switchable entry port 168 through cavity 194 and out of switchable entry port 170 of switching valve assembly 140, into entry and exit port 76 in chamber 68 and out of entry and exit port 78 into switchable entry port 164 through cavity 192 and out of switchable entry port 162 in switching valve assembly 140, through the fluid conduit in mounting block 20 and out of pipette 22 into the receptacle. This path of diluent flow acts to ensure that all the sample drawn into pipette 22 is fully discharged and further acts to wash the interior surfaces of pipette 22 so as to prevent any sample from being mixed with a subsequent sample which may be taken and diluted.

During the same period of upward motion for mounting plate 86, plunger 88 also moves upwardly into its chamber 66. This causes the displacement of the diluent in chamber 66 which exits via both exit and entry ports 74 and 72 into switchable entry ports 172 and 166 respectively of switching valve assembly 140. As these two switchable entry ports communicate through chamber 152, entry port 156 and flexible tubing 200 with the diluent, the diluent displaced from chamber 66 will be coupled back to the source of diluent.

During the movement of eccentric 50 between the positions shown in FIGS. 9 and 10, spool valve member 123 remains stationary in its second position because pivot arm 124 is again freely slidable on eccentric 50 as a result of the elongate slot 126. Between the positions of eccentric 50 shown in FIGS. 10 and 7, mounting plate 86 will be maintained in its first or uppermost position because pivot arm 96 is freely slidable on eccentric 50 as a result of elongate slot 98 in pivot arm 96. During this portion of the rotation of eccentric 50 however, spool valve member 123 will be moved, via eccentric 50 and pivot arm 124, back to its first position. When eccentric pin 50 reaches the position shown in FIG. 7, one of cams 46 and 48 will engage lever arm 54 to opening the contacts of microswitch 52 and interrupting the power supplied to motor 38. Motor 38 will stop rotating thus terminating further clockwise rotation of cam 44 and eccentric 50 and stopping further operation of diluter 10. The entire dilution cycle now has been completed.

As previously noted, a lever (not shown) is secured to microswitch 58 and it extends through an aperture in member 36. This lever bears against the upper surface of mounting plate 86. When mounting plate 86 is in its first or uppermost position, member 86 closes contacts so as to provide current to status lamp 30 thus indicating that diluter 10 is ready to take a sample. When mounting plate 86 is in its second or lower position, the lever arm connected to microswitch 58 is in a second position above and away from the upper surface of mounting plate 86 causing a second set of contacts to be closed in microswitch 58 which supplies current to status lamp 32. This then indicates that diluter 10 is ready to provide a dilution or diluted sample previously taken.

It is believed from the foregoing that the structure of the present invention constitutes a highly effective automatic diluting device which is simple and substantially foolproof in operation. Since sample is drawn into the pipette during the intake stroke and discharged during the discharge stroke followed by a small portion of diluent, the pipette is thoroughly rinsed with diluent following delivery of sample and the danger of a sample contaminating the next dilution is thereby avoided. Furthermore, the use of a pipette to draw the sample and then discharge the sample plus a smaller additional quantity of diluent along with a second nozzle to discharge the major volume of diluent in the same period of time allows the dilution to be made in a shorter period of time without the danger of creating bubbles.

It is to be understood that although the example was shown and described with respect to diluting a sample in a ratio of 1/100ths, the dilution in a ratio of 1/500ths can equally as well be taken by moving dilution knob 34 to its alternate indexing position. In this alternate position, switchable entry ports 162 and 172 are connected via cavity 192 and switchable entry ports 166 and 168 are connected via cavity 194, all of course in switching valve assembly 140. Without reiterating in detail the entire cycle, in operation, a sample will be drawn into pipette 22 which is equal in volume to the volume displaced by retraction or withdrawal of plunger 88 from cylinder 66. This same volume, along with a small portion of the diluent volume of chamber 70 will be discharged when mounting plate 86 is moved back to its first or uppermost position and plunger 88 is fully entered into chamber 66. When chamber 66 is connected via switching valve assembly 140 to pipette 22, chamber 68 is connected via switchable entry ports 164 and 170, entry port 156 and flexible tubing 200 to the source of diluent for drawing in and expelling diluent in accordance with the upward and downward movement of plunger 90 and the corresponding displacement of volume within chamber 68.

Figure 11:
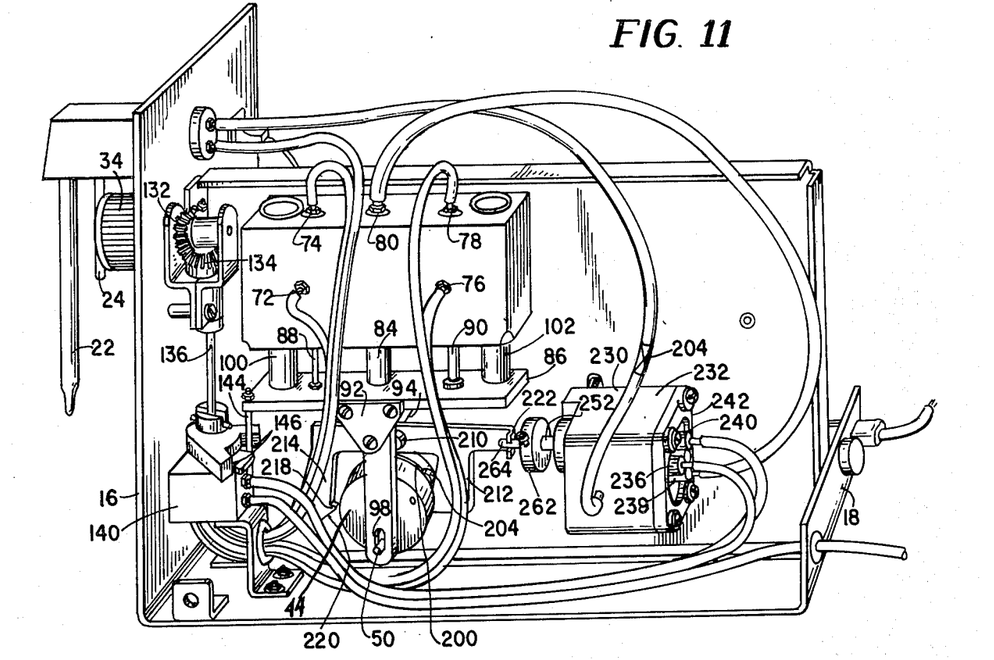
FIG. 11 is a perspective view of an alternate embodiment of the diluter of this invention with the cover off, showing the diluting mechanisms.

In FIG. 11 there is shown an alternate embodiment of the diluter of this invention. The diluter shown in this figure performs the identical functions of the diluter shown in the preceding figures. A substantial portion of the diluter shown in FIG. 11 is identical to the diluter shown in the preceding figures. Those portions which are identical are given identical number designations and will not be described again. Only those portions which are different from the previous embodiment will be described.

Figures 12, 13:
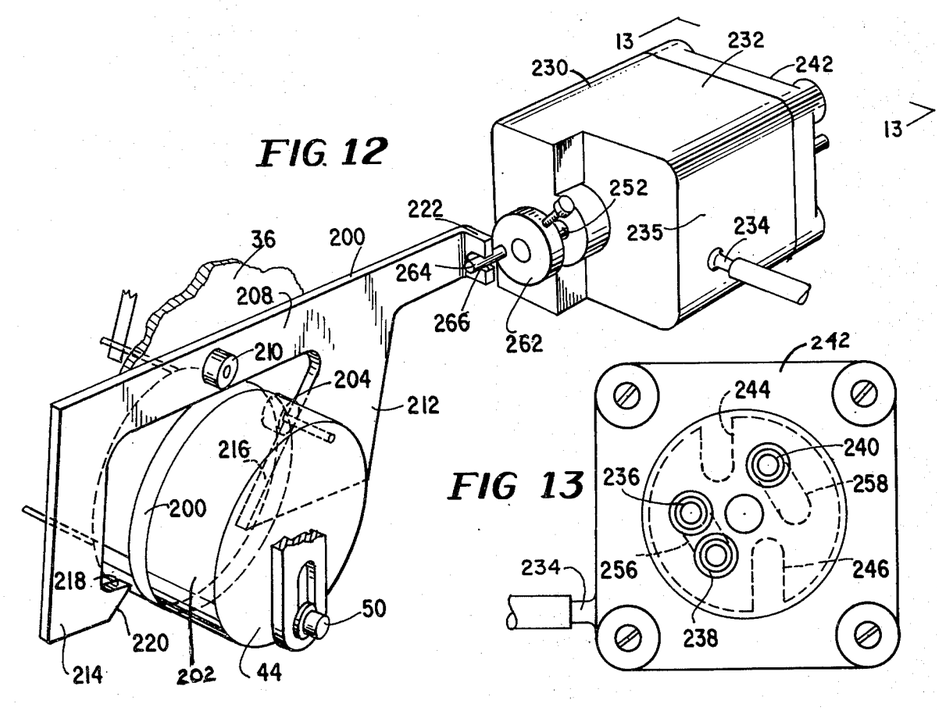
FIG. 12 is a perspective view showing a portion of the diluter embodiment shown in FIG. 11.
FIG. 13 is a plan view of a portion of the diluter shown in FIG. 11 taken in the direction of the arrows 13—13 shown in FIG. 12.

Referring to FIGS. 11 and 12, for both embodiments, cam 44 is shaped in the form of a cylinder with an eccentric 50 located on the top surface. In this embodiment a slot 200 is cut into the side wall 202 of eccentric 44 and extends around the entire circumference. A second eccentric 204 is positioned in slot 202.

A lever 206 includes a first substantially horizontally disposed portion 208 which is pivotally secured to member 36 at pivot 210. Lever 206 includes a first leg 212 which extends downwardly substantially perpendicular to portion 208 and a second leg 214 which also extends downwardly substantially perpendicular to portion 208. First and second legs 212 and 214 are spaced a predetermined distance apart with cam 44 positioned in the space between legs 212 and 214 and portion 208. First leg 212 includes a cam surface 216 which extends at an angle with respect to the vertical plain towards leg 214 and extends into slot 200. Second leg 214 includes a projection 218 with a cam surface 220 thereon. The projection 218 and cam surface 220 also extend into slot 200. Portion 208 extends beyond leg 212 in the horizontal direction, and has a yoke 222 formed at its distal end.

The spool valve housing 110 shown in the previously described embodiment is replaced in this embodiment with a valve assembly 230. Valve assembly 230 is quite similar to switching valve assembly 140 and includes a cube shaped housing 232 defining a central chamber. An entry port 234 is formed in one side wall 235 of housing 232 and communicates with the central chamber. Three switchable entry ports 236, 238, and 240 are formed in side wall 242 of housing 232. Entry ports 236 and 238 are positioned adjacent one another and entry port 240 is positioned radially opposite to entry port 238. Slots 244 and 246 (shown in dotted lines in FIG. 13) are formed on the inner surface of side wall 242 and allow communication with the central chamber. A switching valve rotor assembly (not shown) is positioned in the central cavity and includes a rod shaped 252, a portion of which is shown in FIG. 11 extending from a side wall of housing 232. A disc 262 is secured to the distal end of rod portion 252. Eccentric 264 is secured to disc 262 and seats in a slot 266 of yoke 222. A pair of oval shaped rubber grommets which are substantially the same as grommets 188 and 190 are secured to a surface of a circular plate portion in the valve assembly and define cavities 256 and 258 respectively. Cavities 256 and 258 and the plate edge are shown as dotted lines in FIG. 13.

In operation cam 44 rotates allowing eccentric 204 to move across cam surface 216 on leg 212. The passage of eccentric 204 across cam surface 216 will force leg 212 in an outward and upward direction causing lever 206 to pivot about pivot 210 to a second position. As lever 206 pivots, yoke 222 will move upward causing eccentric 264 to move upward. The movement of eccentric 264 will cause disc 262 and rod portion 252 to rotate approximately 60° to a second position. In this second position, cavity 256 will provide a conduit between entry port 238 and slot 246 and cavity 258 will provide a conduit between entry port 240 and slot 244.

During another portion of the operating cycle cam 44 will rotate so that eccentric 204 will move across cam surface 220 of leg 214. The movement of eccentric 204 across cam surface 220 will force leg 214 outward causing yoke 222 to pivot downward about pivot 210 to the first position. As lever 206 moves from the second to first position slot 266 in yoke 222 will carry eccentric 264 downward. The downward movement of eccentric 264 will cause disc 262 and rod 252 to rotate approximately 60° and move from the second to the first position causing cavities 256 and 258 to rotate approximately 60°. In the first position cavity 256 provides a conduit between entry ports 236 and 238 and entry port 240 is blocked from communicating with the chamber formed by housing 232.

It should be appreciated that during the portion of the rotational cycle of eccentric 50 shown as occurring between the positions in FIGS. 7 and 8 lever 206 and rotor assembly 250 remain stationery in their first position. However, when eccentric 50 reaches the point of rotation shown in FIG. 8 and continues rotating in a clockwise direction, eccentric 204 will cause lever 206 and valve assembly 230 to move to their respective second positions. The second position will be reached and no further movement of lever 206 and valve assembly 230 will occur after eccentric 50 is in the position shown in FIG. 9. It also should be noted at this point that between the positions of eccentric 50 shown in FIG. 8 and FIG. 9 and during movement of lever 206 and valve assembly 230 there will be no additional upward or downward movement of plate 86 and plungers 84, 88, and 90.

When the position shown in FIG. 10 has been reached by rotation of motor 38, just before cams 46 and 48 on the reverse side of member 36 engage lever 54 opening the contacts supplying power to motor 38, eccentric 204 moves across cam surface 220 causing lever 206 and rotor assembly 250 to return to their first positions. Immediately thereafter operation of the apparatus is automatically stopped by lever 54 opening the contacts supplying power to motor 38.

In the first embodiment spool vave 123 changed from in first to its second position just prior to the first half of termination of rotation of cam 44 and eccentric 50, and changed back from its second to its first position just prior to the termination of the second half of rotation of cam 44 and eccentric 50. In this embodiment lever 206 moves from its first to its second position after termination of the rotational cycle of eccentric 50 shown as occurring between the positions shown in FIGS. 8 and 9 and after reinitiation of rotation by actuation of switch activator mechanism 26. Lever 206 is pivoted from its second to its first position at the same time as in the previous embodiment. The difference in timing for movements from the first to second position is of no real consequence because plate 86 remains stationery just prior to termination of the first half of the rotational cycle and after initiation of the second half of the rotational cycle of eccentric 50.

During the downward movement of plate 86 and plunger 84 in chamber 70 diluent will be drawn from a source of diluent through flexible tubing 200, into and out of ports 156 and 154 respectively in switching valve assembly 140, into and out of ports 236 and 238 respectively in valve assembly 230 and through port 80 into diluent chamber 70. Downward movement of plunger 90 will operate in the same manner described with respect to the previous embodiment to draw a quantity of sample into the uncalibrated pipette 22.

Downward movement of plunger 88 will also operate at the same manner as described with respect to the previous embodiment. During this portion of the rotational cycle entry port 240 in valve assembly 230 will be blocked.

During the upward movement of plate 86 and plungers 84, 88, and 90, while lever 206 is in its second position, the diluent displaced in chamber 68 will exit in the same manner was was described with respect to the first embodiment. The diluent displaced in chamber 70 by upward movement of plunger 84 will be expelled via entry and exit port 80, entry port 238, cavity 256 and slot 246 into the chamber formed by housing 232 of valve assembly 230. The diluent entering the chamber formed in housing 232 will force diluent to be expelled via two paths. The first path is out through entry and exit port 234, through choke 204, through a fluid conduit in mounting block 20, and out through nozzle 24 into the waiting receptacle. The second path is from the chamber formed by housing 232 through slot 244 formed in side wall 242 of housing 232, through cavity 258, out of entry port 240, into switchable entry port 168, through cavity 194, out of switchable entry port 170 of switching valve assembly 140, into entry and exit port 76 in chamber 68, out of entry and exit port 78, into switchable entry port 162 in switching valve assembly 140, through the fluid conduit in mounting block 20 and out of pipette 22 into the receptacle. This path of diluent flow acts to insure that all the sample drawn into pipette 22 is fully discharged and further acts to wash the interior surfaces of pipette 22 so as to prevent any sample from being mixed with a subsequent sample which may be taken and diluted.

While in the foregoing we have disclosed the embodiment of the invention in considerable detail for purpose of illustration, it will be understood by those skilled in the art that many of these details may be varied without departing from the spirit and scope of the invention.

What it is claimed and desired to secure by Letters Patent of the United States is:

1. An automatic device for drawing and diluting a first sample with a diluent wherein the sample and diluent are mixed in a precise ratio, including in combination,
   a diluent chamber having a first reciprocable plunger therein,
   a first sample chamber having a second reciprocable plunger therein,
   coupling means coupled to said first and second plungers for moving said plungers an equal distance in said chambers, drive means including a motor having a rotating drive, cam means secured to said motor rotating drive and rotating therewith, said cam means having an eccentric thereon coupled to said coupling means for reciprocating said coupling means between first and second positions whereby said plungers are reciprocally moved equal distances,
   said coupling means including eccentric follower means for following rotation of said eccentric, said eccentric follower means reciprocating said coupling means during first particular portions of each rotation of said cam and said eccentric for moving said coupling means to one of said first and second positions, said coupling means maintaining said first and second positions during second particular portions of each rotation of said cam and said eccentric,
   said first plunger when moved in said diluent chamber displacing a first volume therein, said second plunger when moved in said sample chamber displacing a second volume therein, said first and second volumes having a fixed precise ratio with respect to one another for any equal distance moved by said first and second plungers in said chambers,
   a valve assembly having a valve chamber coupled to said diluent chamber,
   diluent intake passage means and diluent discharge passage means coupled to said valve assembly,
   said valve assembly including a valve member shiftable between a first position wherein said valve chamber couples said diluent intake passage means to said diluent chamber, and a second position wherein valve chamber couples said diluent discharge passage means to said diluent chamber, and
   shifting means coupling said valve member to said eccentric for shifting said valve member between said first and second positions during said second particular portions of each rotation of said cam and eccentric.

2. The device of claim 1 further including stop means for stopping rotation after said valve member shifts between said first and second positions.

3. An automatic diluting device for drawing and diluting a first sample with a diluent wherein the sample and diluent are mixed in a precise ratio, including in combination:
   a diluent chamber having a first reciprocable plunger therein,
   a first sample chamber having a second reciprocable plunger therein,
   a second sample chamber having a third reciprocable plunger therein, coupling means coupled to said first, second and third plungers for moving the said plungers an equal distance in said chambers, said first plunger when moved in said diluent chamber displacing a first volume therein, said second plunger when moved in said sample chamber displacing a second volume therein, said third plunger when moved in said second sample chamber displacing a third volume therein, said first and second volumes having a fixed precise ratio with respect to one another for any equal distance moved by said first and second plungers in said chambers, said first and third volumes having a fixed precise ratio with respect to one another for any equal distance moved by said first and third plungers in said diluent chamber and second sample chamber, said coupling means reciprocating between first and second positions for reciprocating said first, second and third plungers within their chambers, sample intake and discharge passage means and diluent intake passage means, a switching valve assembly coupled to said sample intake and discharge means and to said first and second sample chambers, said switching valve assembly having a first switching position for coupling said sample intake and discharge passage means to said first sample chamber and said diluent intake passage means to said second sample chamber, and a second switching position for coupling said sample intake and discharge passage means to said second sample chamber and said diluent intake passage means to said first sample chamber.

4. The device of claim 3 further including, diluent discharge passage means, a valve assembly having a valve chamber coupled to said diluent chamber, said switching valve assembly and said diluent discharge passage means being coupled to said valve assembly, said valve assembly including a valve member shiftable between a first position wherein said valve chamber couples said diluent chamber to said diluent intake passage means through said switching valve assembly in either of said first and second switching positions of said switching valve assembly, and a second position wherein said valve chamber couples said diluent discharge passage means to said diluent chamber.

5. The device of claim 4 wherein said diluent discharge passage means is coupled to said first sample chamber when said switching valve assembly is in said first position and said valve assembly is in said second position and said diluent discharge passage means is coupled to said second sample chamber when said switching valve assembly is in said second position and said valve assembly is in said second position.

6. The device of claim 4 wherein said switching valve assembly includes, a housing defining a chamber, a first port in said housing for coupling said chamber to said diluent intake passage means, a second port in said housing for coupling said chamber to said valve assembly, a plurality of switching ports, at least one switchable connection means positioned in said chamber and providing a closed path between at least a first and a second of said plurality of switching ports, said switchable connection means being switchable between at least one of said first and second switching ports and a third switching port.

7. The device of claim 6 wherein said switchable connection means includes, conduit means secured to a rotatable member positioned in said chamber and forming said closed path said switchable connection means being switchable between at least a first and second position for switching said conduit means between at least one of said first and second switching ports and said third switching port.

8. The device of claim 7 wherein said plurality of switching ports unconnected via said closed path communicate with said chamber and said first and second ports.

9. An automatic diluting device for drawing and diluting a first sample with a diluent and wherein the sample and diluent are mixed in precise ratio including in combination, a diluent chamber having a first plunger therein reciprocable between a first and a second position for displacing a first volume therein when moved, a first sample chamber having a second plunger therein reciprocable between a first and a second position for displacing a second volume therein when moved, said first and second volumes arranged to have a fixed precise ratio with respect to one another for any equal distance moved by said first and second plungers in their chambers, sample intake and discharge passage means coupled to said first sample chamber, said sample intake and discharge passage means coupled to said sample for drawing a sample therein during movement of said second plunger between said first and second positions, and discharging said sample during movement of said second plunger between said second and first positions, diluent intake passage means coupled to said diluent chamber for drawing diluent therein during movement of said first plunger between said first and second positions, diluent discharge passage means coupled to said diluent chamber for discharging diluent during movement of said first plunger between said second and first positions, coupling means coupled to said first and second plungers for simultaneously reciprocally moving same an equal distance in said chambers between said first and second positions, said sample intake and discharge passage means including means for discharging said sample at a first velocity in a first period of time and said diluent discharge passage means including means for discharging said diluent at a second lower velocity in said first period of time for preventing splashing and bubbles.

10. An automatic diluting device for drawing and diluting a first sample with a diluent and wherein the sample and diluent are mixed in precise ratio including in combination, a diluent chamber having a first plunger therein reciprocable between a first and a second position for displacing a first volume therein when moved, a first sample chamber having a second plunger therein reciprocable between a first and a second position for displacing a second volume therein when moved, said first and second volumes arranged to have a fixed precise ratio with respect to one another for any equal distance moved by said first and second plungers in their chambers, sample intake and discharge passage means coupled to said first sample chamber, said sample intake and discharge passage means coupled to said sample for drawing a sample therein during movement of said second plunger between said first and second positions, and discharging said sample during movement of said second plunger between said second and first positions, diluent intake passage means coupled to said diluent chamber for drawing diluent therein during movement of said first plunger between said first and second positions, diluent discharge passage means coupled to said diluent chamber for discharging diluent during movement of said first plunger between said second and first positions, coupling means coupled to said first and second plungers for simultaneously reciprocally moving same an equal distance in said chambers between said first and second positions, said diluent discharge passage means including a first diluent discharge path for discharging a first large portion of the diluent, and a second diluent discharge passage for discharging a second small portion of the diluent, said second small path being coupled to said sample intake and discharge passage means for discharging said second small portion therethrough during movement of said first and second plungers between said second and first positions.

11. The device of claim 10 wherein said second diluent discharge path is coupled to said sample chamber for coupling said second small portion of diluent therethrough to said sample intake and discharge passage means.

12. An automatic diluting device for drawing and diluting a first sample with a diluent and wherein the sample and diluent are mixed in precise ratio including in combination, a diluent chamber having a first plunger therein reciprocable between a first and a second position for displacing a first volume therein when moved, a first sample chamber having a second plunger therein reciprocable between a first and a second position for displacing a second volume therein when moved, a second sample chamber having a third plunger therein reciprocable between a first and a second position for displacing a third volume therein when moved, said first and second volumes arranged to have a fixed precise ratio with respect to one another for any equal distance moved by said first and second plungers in their chambers, said first and third volumes arranged to have a fixed precise ratio with respect to one another for any equal distance moved by said first and third plungers in said chambers, sample intake and discharge passage means, switch means coupling said sample intake and discharge means to said first and second sample chambers for selectively switching said sample intake and discharge passage means to one of said first and second sample chambers, said sample intake and discharge passage means being coupled to said sample for drawing a sample therein during movement of said second and third plungers between said first and second positions, and discharging said sample during movement of said plungers between said second and first positions, diluent intake passage means coupled to diluent chamber for drawing diluent therein during movement of said first plunger between said first and second positions, diluent discharge passage means coupled to said diluent chamber for discharging diluent during movement of said first plunger between said second and first positions, and coupling means coupled to said first, second and third plungers for simultaneously reciprocally moving said plungers an equal distance in said chambers between said first and second positions.

13. The device of claim 12 wherein said switch means is further coupled between said diluent intake passage means and said diluent chamber, and further couples said diluent intake passage means to said first sample chamber when said sample intake and discharge passage means is coupled to said second sample chamber, and couples said diluent intake passage means to said second sample chamber when said sample intake and discharge passage means is coupled to said first sample chamber.

14. The device of claim 13 further including a valve means coupling said diluent chamber, said switching means and said diluent discharge passage means, said valve means being operable to couple said diluent chamber to said switch means for receiving diluent therefrom during movement of said first plunger between said first and second positions, and couple said diluent chamber to said diluent discharge passage means during movement of said first plunger between said second and first positions for discharging diluent, said valve means being further operative to couple said switch means to said diluent discharge passage means during movement of said second and third plungers between said second and first positions for coupling said diluent to said sample intake and discharge passage means.

15. The device of claim 14 further including driving means coupled to said coupling means for reciprocating said coupling means whereby said first, second and third plungers are reciprocally moved between said first and second positions.

16. The device of claim 14 wherein said coupling means includes a mounting plate for mounting said first, second and third plungers, and driving means coupled to said mounting plate for reciprocating said mounting plate whereby said first, second and third plungers are simultaneously moved equal distances within said chambers, and between said first and second positions.

17. The device of claim 16 wherein said diluent chamber and first and second sample chamber are formed in a single housing, said housing having guiding apertures formed therein, said mounting plate further including guide means secured to said mounting plate, said guide means being positioned in said housing guide apertures and reciprocable therein.

18. The device of claim 17 wherein said driving means includes a motor for providing a rotating drive, cam means secured to said motor rotating drive and rotating therewith, said cam means having an eccentric thereon coupled to said mounting plate for reciprocating said mounting plate in said guide apertures.

19. An automatic diluting device for drawing and diluting a first sample with a diluent and wherein the sample and diluent are mixed in precise ratio including in combination,
- a diluent chamber having a first plunger therein reciprocable between a first and a second position for displacing a first volume therein when moved,
- a first sample chamber having a second plunger therein reciprocable between a first and a second position for displacing a second volume therein when moved,
- said first and second volumes arranged to have a fixed precise ratio with respect to one another for any equal distance moved by said first and second plungers in their chambers,
- sample intake and discharge passage means coupled to said first sample chamber, said sample intake and discharge passage means coupled to said sample for drawing a sample therein during movement of said second plunger between said first and second positions, and discharging said sample during movement of said second plunger between said second and first positions,
- diluent intake passage means coupled to said diluent chamber for drawing diluent therein during movement of said first plunger between said first and second positions,
- diluent discharge passage means coupled to said diluent chamber for discharging diluent during movement of said first plunger between said second and first positions, and
- valve means coupled to said diluent chamber, said diluent intake passage means and said diluent discharge passage means, said valve means being operative to couple said diluent chamber to said diluent intake passage means during movement of said first plunger between said first and second positions and couple said diluent chamber to said diluent discharge passage means during movement of said first plunger between said second and first positions, said valve means being further operative to couple said diluent discharge passage means to said sample intake and discharge passage means during movement of said first plunger between said second and said first positions.

20. The automatic diluting device of claim 19 further including,
- drive means having a rotating motor,
- cam means secured to said rotating motor and rotating therewith,
- a lever in communication with said cam means and coupled to said valve means, said lever being pivotable to a first position and second position during movement of said plunger between said second and first positions,
- said valve means being operative in response to pivoting of said lever to said first position to couple said diluent chamber to said diluent intake passage means and operative in response to pivoting of said lever to said second position to couple said diluent chamber to said diluent discharge passage means and to couple said diluent discharge passage means to said sample intake and discharge passage means.

21. The automatic diluting device of claim 20 further including, coupling means coupled to said first and second plungers for moving said plungers an equal distance in said chambers, said cam means including a first eccentric coupled to said coupling means for reciprocating said coupling means between said first and second positions whereby said plungers are reciprocably moved equal distances and a second eccentric communicating with said lever for pivoting said lever to said first and second positions during movement of said plungers between said second and first positions.

22. The automatic diluting device of claim 21 wherein said lever includes, first and second cam surfaces, said lever pivoting to said second position when said second eccentric moves across said first cam surface and to said first position when said second eccentric moves across said second cam surface.

23. The automatic diluting device of claim 22 wherein said lever includes, a first portion pivotally secured to said diluting device, a first and second leg extending substantially at right angles to said first portion, said first cam surface being on said first leg and said second cam surface being on said second leg.

24. The automatic diluting device of claim 23 wherein said cam means is cylindrical, said second eccentric being secured at said cylinder side wall, said cam means being positioned between said first and second legs whereby said second eccentric communicates with said first and second cam surface on said first and second legs during rotation.

25. The automatic diluting device of claim 24 wherein said cam means has a slot cut into the cylindrical side wall around the entire circumference, said second eccentric being secured in said slot and said first and second legs of said lever being positioned in said slot whereby said second eccentric alternately communicates with said first and second cam surfaces upon rotation of said cam means.

26. The automatic diluting device of claim 23 wherein said lever first portion is coupled to said valve means.

27. The automatic diluting device of claim 20 wherein said valve means include means for rotating to a first position in response to pivoting of said lever to said first position and for rotating to a second position in response to pivoting of said lever to said second position, said valve means being operative when rotated to said first position to couple said diluent chamber to said diluent intake passage means and operative when rotated to said second position to couple said diluent chamber to said diluent discharge passage means and to couple said diluent discharge passage means to said sample and intake and the discharge means.

* * * * *